(12) United States Patent
Mailyan

(10) Patent No.: US 7,955,075 B2
(45) Date of Patent: Jun. 7, 2011

(54) DEVICE FOR CORRECTION OF THE FORM OF DENTAL ALVEOLAR ARCH

(75) Inventor: Pavel D. Mailyan, Yerevan (AM)

(73) Assignee: Mayadontics LLC, Novato, CA (US)

( * ) Notice: Subject to any disclaimer, the term of this patent is extended or adjusted under 35 U.S.C. 154(b) by 47 days.

(21) Appl. No.: 11/327,212

(22) Filed: Jan. 7, 2006

(65) Prior Publication Data

US 2007/0037110 A1 Feb. 15, 2007

(30) Foreign Application Priority Data

Aug. 9, 2005 (AM) .................................. 20050147

(51) Int. Cl.
*A61C 3/00* (2006.01)
(52) U.S. Cl. ................................. 433/7; 433/6
(58) Field of Classification Search .................. 433/6, 7, 433/18, 24, 20–21
See application file for complete search history.

(56) References Cited

U.S. PATENT DOCUMENTS

| | | | | |
|---|---|---|---|---|
| 1,142,467 A | | 6/1915 | Walker | 433/21 |
| 4,026,023 A | | 5/1977 | Fisher | 433/7 |
| 4,028,808 A | | 6/1977 | Schwartz | 433/7 |
| 4,123,844 A | | 11/1978 | Kurz | |
| 4,468,196 A | * | 8/1984 | Keller | 433/24 |
| 4,571,178 A | * | 2/1986 | Rosenberg | 433/18 |
| 4,573,914 A | | 3/1986 | Nord | 433/18 |
| 4,637,796 A | * | 1/1987 | Korn | 433/7 |
| 4,976,614 A | * | 12/1990 | Tepper | 433/18 |
| 5,002,485 A | | 3/1991 | Aagesen | 433/7 |
| 5,087,196 A | * | 2/1992 | Polanco | 433/7 |
| 5,096,416 A | * | 3/1992 | Hulsink | 433/6 |
| D342,318 S | * | 12/1993 | Moffat | D24/180 |
| 5,376,001 A | * | 12/1994 | Tepper | 433/6 |
| 5,399,087 A | | 3/1995 | Arndt | 433/7 |
| 5,507,638 A | | 4/1996 | Strazielle | 433/6 |
| 5,536,169 A | * | 7/1996 | Yousefian | 433/6 |
| 5,580,243 A | | 12/1996 | Bloore | 433/6 |
| 5,697,781 A | | 12/1997 | Ellingson | 433/18 |
| 5,769,631 A | * | 6/1998 | Williams | 433/7 |
| 5,785,520 A | * | 7/1998 | Carano et al. | 433/7 |
| 5,829,970 A | | 11/1998 | Yousefian | 433/7 |

(Continued)

FOREIGN PATENT DOCUMENTS

AM 197 11/1996

(Continued)

OTHER PUBLICATIONS

Fitting. (n.d.). Dictionary.com Unabridged. Retrieved Oct. 19, 2010, from Dictionary.com website: http://dictionary.reference.com/browse/fitting.*

(Continued)

*Primary Examiner* — Cris L Rodriguez
*Assistant Examiner* — Heidi M Eide
(74) *Attorney, Agent, or Firm* — Joshua D. Isenberg; JDI Patent

(57) ABSTRACT

A device has a metal wireframe with two lateral fastening elements which are connected through metal lingual and vestibular springs to a frontal fastening element and executed in the form of metal wireframes clasping teeth of dentition's lateral segments and performed of lingual and vestibular details located at necks of teeth from the one side and dispersedly mounted along the height of teeth from the other side and connected by crosspieces.

14 Claims, 3 Drawing Sheets

U.S. PATENT DOCUMENTS

| | | | | |
|---|---|---|---|---|
| 6,032,677 | A | 3/2000 | Blechman | 128/899 |
| 6,033,216 | A * | 3/2000 | Souris | 433/7 |
| 6,435,871 | B1 * | 8/2002 | Inman | 433/7 |
| 7,104,790 | B2 * | 9/2006 | Cronauer | 433/6 |
| 7,192,281 | B2 | 3/2007 | Mailyan | 433/215 |
| 2003/0104335 | A1 * | 6/2003 | Chung | 433/18 |
| 2004/0009449 | A1 | 1/2004 | Mah et al. | |
| 2004/0013993 | A1 * | 1/2004 | Ito | 433/6 |
| 2004/0048222 | A1 | 3/2004 | Forster et al. | |
| 2005/0019720 | A1 * | 1/2005 | Harima | 433/18 |
| 2005/0037312 | A1 * | 2/2005 | Uchida | 433/6 |

FOREIGN PATENT DOCUMENTS

| | | |
|---|---|---|
| AM | 199 | 11/1996 |
| AM | 511 | 3/1999 |
| AM | 512 | 3/1999 |
| AM | 514 | 3/1999 |
| RU | 1412764 | 5/2006 |
| SU | 848020 | 7/1981 |
| WO | WO 2005/048868 | 6/2005 |

OTHER PUBLICATIONS

A. A. Kolesov "Stomatology of childhood" Moscow 1970, pp. 452, 453 (description of Fig. 106).
Kishinev, *Directory on Orthodontics*, p. 178 (description of Fig. 27) and pp. 179, 179, 181, 182 (description of Fig. 28), 188 and 189; 1990.
U.S. Appl. No. 11/327,209, to Pavel D. Mailyan, filed Jan. 7, 2006.
U.S. Appl. No. 11/327,210, to Pavel D. Mailyan, filed Jan. 7, 2006.
U.S. Appl. No. 11/327,211, to Pavel D. Mailyan, filed Jan. 7, 2006.
Final Office Action of U.S. Appl. No. 11/327,210 dated Apr. 14, 2008.
Non-Final Office Action dated Aug. 18, 2008—U.S. Appl. No. 11/327,210, 9 pages.
L. S. Persin, "Orthodontia—Treatment of Dentimaxillary Anomalies", Moscow, Scientific publishing center "Inzhener" 1988, pp. 15-17—Russian version.
L. S. Persin, "Orthodontia—Treatment of Dentimaxillary Anomalies", Moscow, Scientific publishing center "Inzhener" 1988, pp. 15-17—English translation.
William R. Proffit et al., Contemporary Orthodontics, Fourth Edition, 2007, Chapter 10—"Mechanical Principles in Orthodontic Force Control", pp. 373-377.
Office Action dated Mar. 31, 2009 for U.S. Appl. No. 11/327,210, 6 pages.
An English translation of a Response to the Examiners of the Russian Patent Office dated May 6, 2009 for the Russian Patent Application No. 2008105370 (International Application No. PCT/US2006/028793), 5 pages.
Extended European Search Report dated Oct. 27, 2009 for European Patent Application No. 06788389.2.
Non-final Office Action dated Oct. 26, 2009 for U.S. Appl. No. 11/327,210.
Office Action dated Jul. 5, 2006 of U.S. Appl. No. 11/327,209 issued as US patent 7,192,281.
Notice of Allowance dated Jan. 22, 2007 of U.S. Appl. No. 11/327,209 issued as US patent 7,192,281.
Office Action dated Aug. 1, 2007 of U.S. Appl. No. 11/327,210.
Office Action dated Aug. 1, 2007 of U.S. Appl. No. 11/327,211.
"The International Search Report" and "The Written Opinion of the International Searching Authority" dated Sep. 13, 2007 for International application No. PCT/US2006/028793.
Final Office Action dated Jan. 22, 2009 for U.S. Appl. No. 11/327,210.
Notice of Allowance dated Feb. 4, 2008 of U.S. Appl. No. 11/327,211 issued as US patent 7,357,633.
Definition of word "Crown"—Parts of Your Teeth and Gums from Simple Steps to Better Dental Health—download from http://www.simplestepsdental.com/SS/ihtSS/r.WSIHW/st.31843/t.31883/pr.3.html on Mar. 15, 2010, 2 pages.
Robert Marzban et al.—"Slow Maxillary Expansion with Nickel Titanium"—JCO/Aug. 1999, vol. XXXIII No. 8, pp. 431-441.
Handelman et al—"Nonsurgical Rapid Maxillary Expansion in Adults: Report on 47 Cases Using the Haas Expander"—Angle Orthodontist, vol. 70, No. 2, 2000, pp. 129-144.
Aldo Carano—"Effect of different force levels on the midpalatine suture"—Progress in Orthodontics, vol. 2, Issue 1, pp. 30-41, Jan. 2001—English Abstract only.
"Active Plate—Haas Expander-Fixed-Upper" download on Aug. 17, 2010 from http://www.northstardental.com/our-products-and-services/active-plates/haas-expander-fix, 2 pages.
Kiliç et al.—"A comparison of dentoalveolar inclination treated by two palatal expanders"—European Journal of Orthodontics 30 (2008) 67-72.
Dr. Steve G—"Low-Cost Nighttime Tooth Alignment: A Powerful Way to Attract New Patients!"—NightShift Ortho : Orthodontics : Straight Teeth : Retainers : Braces : Invisible Braces—download on Aug. 9, 2010 from http://www.nightshiftortho.com/doctors.html, 10 pages.
Graber-Vanasdall-Vig—"Orthodontics—Current Principle & Technique"—Fourth Edition—Chapter 3—Treatment of Patients in Mixed Dentition, pp. 547-550.
"Nitanium® Palatal Expander2TM", Ortho Organizers. 2004 Precision Orthodontics Ltd, 13 pages.
Gerson Luiz Ulema Ribeiro et al.—"Palatal Expansion With Six Bands: an alternative for young adults"—Rev. Clin. Pesq. Odontol., Curitiba, v. 5, n. 1, p. 61-66, Jan. 2009.
Laser Welding by LASERTEK—download on Sep. 1, 2010 from http://www.fabdent.com/lasertek/gallery_r.html.
"Fitted"—Definition and More from the Free Merriam-Webster Dictionary—download on Aug. 30, 2010 from http://www.merriam-webster.com/dictionary/fitted.
Amparo Castañer Peiro—"Interceptive orthodontics: The need for early diagnosis and treatment of posterior crossbites"—Clinical Dentistry—Interceptive orthodontics—Med Oral Patol Oral Cir Bucal 2006;11:E210-4.
Final Office Action dated Apr. 22, 2010 issued for U.S. Appl. No. 11/327,210.
Bloore Appliance Advertising, Finishing Appliances, p. 28—Spring Aligners from <http://www.greatlakesortho.com/content/files/catalogs/laboratory/1126119660.pdf> downloaded Jul. 22, 2010.
Notice of Allowance and Fee(s) Due dated Oct. 6, 2010 issued for U.S. Appl. No. 11/327,210.

* cited by examiner

DEVICE FOR CORRECTION OF THE FORM OF DENTAL ALVEOLAR ARCH

CLAIM FOR BENEFIT OF PRIORITY OF FORIEGN APPLICATION

This application claims the benefit of priority of Republic of Armenia Patent Application No. P20050147, to Pavel D. Mayilyan, filed Aug. 9, 2005 the disclosures of which are incorporated herein by reference.

CROSS REFERENCE TO RELATED APPLICATIONS

This application is related to commonly assigned co-pending U.S. patent application Ser. No. 11/327,211 to Pavel D. Mayilyan entitled "DEVICE FOR CORRECTION OF THE FORM OF UPPER JAW", which is filed concurrently herewith. This application is also related to commonly assigned co-pending U.S. patent application Ser. No. 11/327,209 to Pavel D. Mayilyan entitled "METHOD FOR STIMULATION OF GROWTH OF MISSING TISSUES OF JAW DEFECTS AND A DEVICE FOR ITS REALIZATION", which is filed concurrently herewith. This application is also related to commonly assigned co-pending U.S. patent application Ser. No. 11/327,210 to Pavel D. Mayilyan entitled " METHOD FOR CORRECTION OF THE FORM OF DENTAL ALVEOLAR ARCH ", which is filed concurrently herewith and which is incorporated herein by reference.

FIELD OF THE INVENTION

The invention relates to the medicine and can be used in orthodontics for correction of the form of dental alveolar arch towards its both increase and decrease.

BACKGROUND

As far back as 1880, Continuous has designed a device constituting vestibular and lingual arches connected with each other by crosspieces in the region of lateral teeth. (see, CONSUMMATE OCCLUSION, Robert Murray Ricketts, 1996; FIG. 2-2).

Also known is a device executed in the form of lingual and vestibular springs acting upon frontal teeth and fastened on a lingual arch connecting fastening elements of wireframes on separate lateral teeth (see, U.S. Pat. No. 1,142,467, Aug. 6, 1915).

The devices described above provide correction of teeth in a frontal section, but in view of a rigid attachment of arches to wireframes of lateral teeth, they are characterized by limited opportunities for transversal movement of the latter.

There are also known nonremovable orthodontic devices constituting arches fastened in retainers rigidly fixed on teeth. The mentioned devices allow to provide a correction of the form of dental arch and position of separate teeth via forward-rotary influences on teeth. (see, PCT application No. WO 048868 A2, A61C7/14 Feb. 6, 2005).

The above-mentioned arch devices do not stimulate intensive growth of the alveolar process and correction of the form of dental alveolar arch, owing to which the terms of treatment are prolonged.

Moreover, during the teeth movement, the surface of the alveolar process wall adjacent to the tooth root is periodically exposed to intensive resorption in places of squeezing.

An orthodontic device for correction of dental arches (see, the patent of the Republic of Armenia No. 512. A61C7/00, 1999) on its technical essence is closest to the claimed variants of devices.

The device consist of fastening elements, which are connected through lingual and vestibular arches with activation units and executed in the form of metal wireframes clasping teeth of dentition's lateral segments . The latter are performed of wire details located at necks of teeth from the lingual side and dispersedly mounted along the height of teeth from the vestibular side and connected by crosspieces disposed in interdental spaces.

The design of the device provides corpus (bodily) shifting of teeth: lateral teeth—by forward-rotary influences on them, and frontals—by efforts of vestibular and lingual arches dispersed along the height of incisors. Since the device is removable, there is an opportunity to periodically renew forces exerted by wireframes and arches and decreasing in the course of time through removal of the device and activation of its elements.

Practical use of the device allows to achieve a corpus (bodily) shifting of teeth and increase in transversal dimensions of an alveolar process with the intensity of 0,3-0,4 mm per month. However, the given device has the limited opportunities in realization of sagittal-transversal shifting of teeth and is actually deprived of an opportunity to stimulate the growth of an alveolar process in case of a jaw constriction in the lingual direction. Moreover, the design of the device does not provide stable dispersal of arches along the height of incisors, which results in decrease of the treatment intensity, owing to necessity of the frequent correction of arches.

SUMMARY

The task of the claimed group of inventions is to create designs of devices capable to intensify a correction process of the form of alveolar process and a dental arch.

In accordance with a first embodiment, a device for correction of the form of dental alveolar arch may comprise two or more lateral fastening elements that are connected through metal lingual and vestibular activation units to a frontal fastening element. The lateral and frontal fastening elements may be in the form of metal wireframes adapted respectively to clasp teeth of dentition's lateral and frontal segments, and comprised of lingual and vestibular details adapted to be located at necks of teeth from the one side and adapted to be dispersedly mounted along the height of teeth from the other side. The lingual and vestibular details are connected to each other by crosspieces.

In accordance with a second embodiment of the invention, a device for correction of the form of dental alveolar arch may comprise two lateral fastening elements and a frontal fastening element that are connected to a lingual arch. The lateral fastening elements may be connected to the lingual arch by activation units and at least one of the lateral fastening elements may be additionally connected to the lingual arch by one or more additional springs. The lateral fastening elements and frontal fastening elements may be in the form of metal wireframes respectively adapted to clasp teeth of dentition's lateral and frontal segments. The lateral and frontal fastening elements may include lingual and vestibular details adapted to be located at necks of teeth from the one side and adapted to be dispersedly mounted along the height of teeth from the other side and connected by crosspieces. The frontal fastening element may be connected with the lingual arch directly and/or through springs.

In accordance with a third embodiment of the invention a device for correction of the form of dental alveolar arch may comprise two lateral fastening elements and a frontal fastening element that are connected to a lingual arch. The lateral fastening elements are connected to the lingual arch by activation units located at ends of the lingual arch. The lateral fastening elements and frontal fastening elements may be in the form of metal wireframes respectively adapted to clasp teeth of dentition's lateral and frontal segments. The lateral and frontal fastening elements may be comprised of lingual and vestibular details adapted to be located at necks of teeth from the one side and adapted to be dispersedly mounted along the height of teeth from the other side and connected by crosspieces. The frontal fastening element may be connected with the lingual arch through springs. One or more of the lateral fastening elements may be connected with the frontal fastening element and additionally connected with the lingual arch through one or more additional springs.

The nature of all is such that lingual or vestibular details of metal wireframes dispersed along the height of teeth may be mounted from a side of the teeth facing toward a direction of movement of the teeth.

The nature of all variants of the claimed group of inventions is also that a metal wireframe is performed of components disposed on a separate tooth and/or group of teeth of a segment and connected with each other via lingual and/or vestibular springs.

BRIEF DESCRIPTION OF THE DRAWINGS

The group of inventions is explained by the drawings, where first, second and third variants of the device execution are accordingly represented on FIGS. 1, 2, 3, and a version of the execution of the group of inventions, where a metal wireframe has separate components disposed on two groups of teeth of a lateral segment and connected with each other via lingual and vestibular springs is represented on FIG. 4. Zones of squeezing and tension of an alveolar process, which are formed under influence of a metal wireframe with details dispersedly mounted along the height of a tooth, are depicted on FIGS. 5, 6. The zones of squeezing and tension of an alveolar process in the case of removal of forces exerted by the device, and partial return of a tooth to an initial position are represented in FIG. 7.

DETAILED DESCRIPTION

Figure 1:
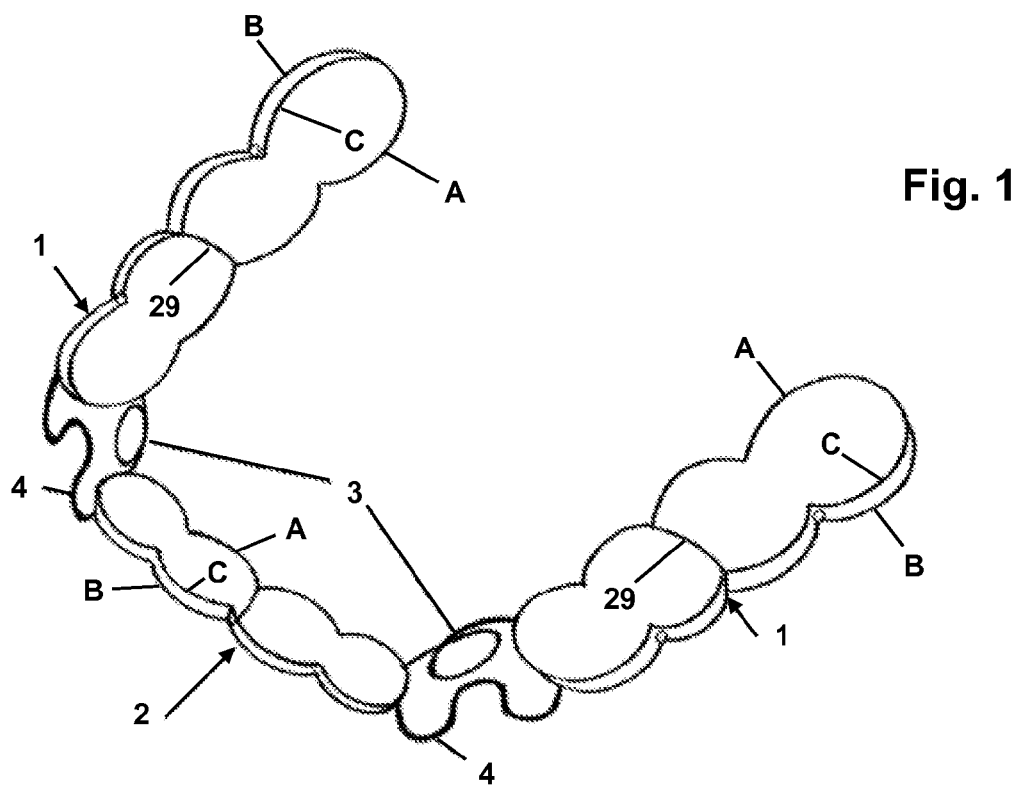

As shown in FIG. 1, a device for correction of the form of dental alveolar arch, in accordance with a first variant of the execution, has fastening elements (1) in the form of metal wireframes clasping teeth of dentition's lateral segments and a metal wireframe (2) mounted on a teeth of dentition's frontal segment, which is connected with fastening elements by lingual springs (3) and/or vestibular springs (4).

Figure 2:
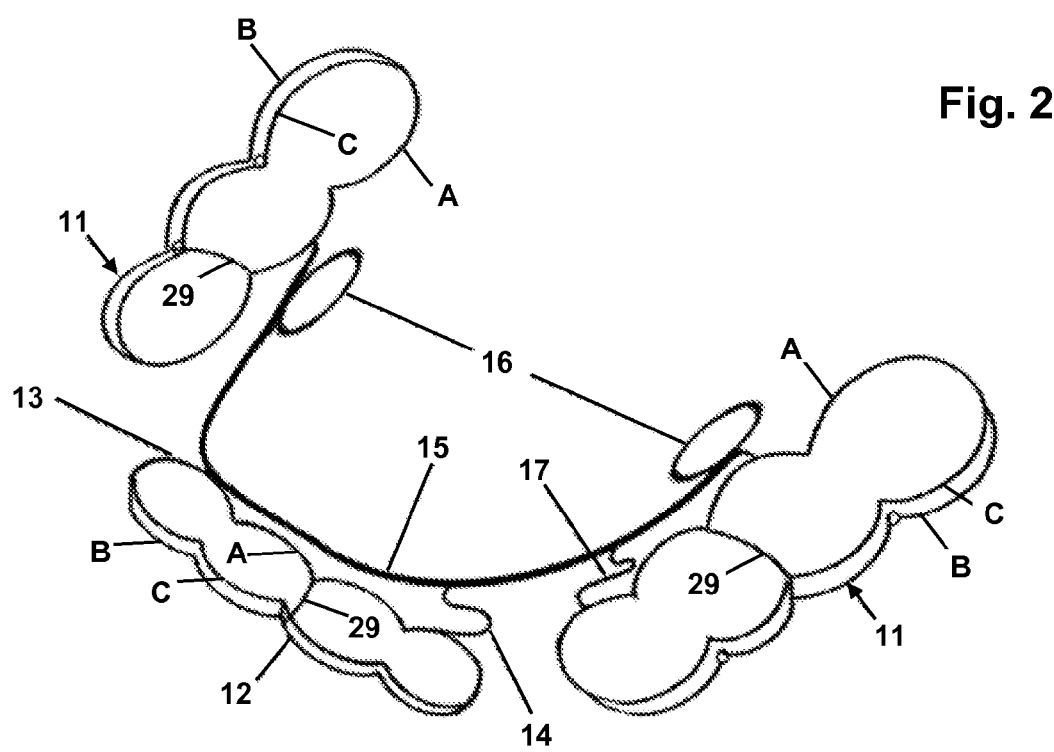
Figure 4:
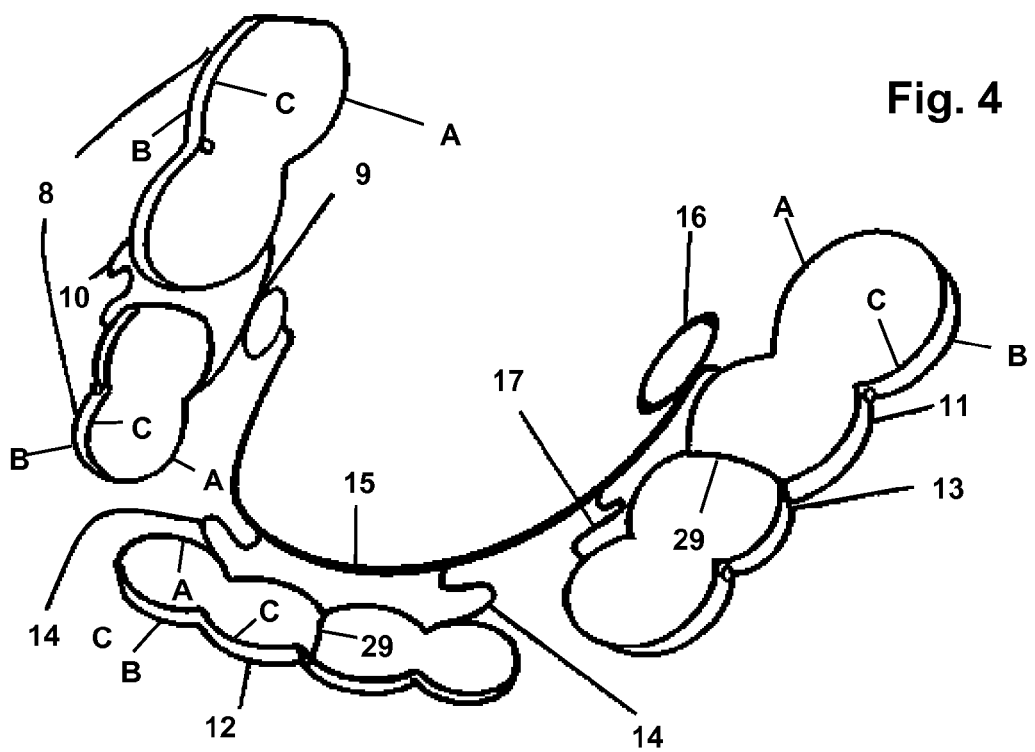

As shown in FIG. 2, a device for correction of the form of dental alveolar arch, in accordance with a second variant of the execution, has fastening elements (11), in the form of metal wireframes clasping teeth of dentition's lateral segments and a metal wireframe (12) mounted on teeth of dentition's frontal segment. The latter is connected directly (13) and/or through spring (14) with a lingual arch (15), the ends of which are fixed on fastening elements (11). The lingual arch (15) has activation units (16) and is additionally connected with one or two fastening elements (11) through springs (17). The performance of the metal wireframe in the form of separate components (see, FIG. 4) may be a version of the proposed variants and in particular of the second variant.

In this case, the component wireframes (8) clasping a separate tooth and/or group of teeth of a segment are connected with each other via lingual springs (9) and vestibular springs (10).

A device for correction of the form of dental alveolar arch, in accordance with a third variant of the execution, has fastening elements (21), in the form of metal wireframes clasping teeth of dentition's lateral segments and a metal wireframe (22) mounted on teeth of dentition's frontal segment. The latter is connected with a lingual arch (24) through springs (23), and the ends of a lingual arch (24) are fixed on the fastening elements (21). The lingual arch (24) has activation units (25) and is additionally connected with the fastening element or elements (21) through springs (26). The metal wireframe (22) of frontal segment in its turn is connected with the fastening element or elements (21) through a spring or springs (27).

Figure 3:
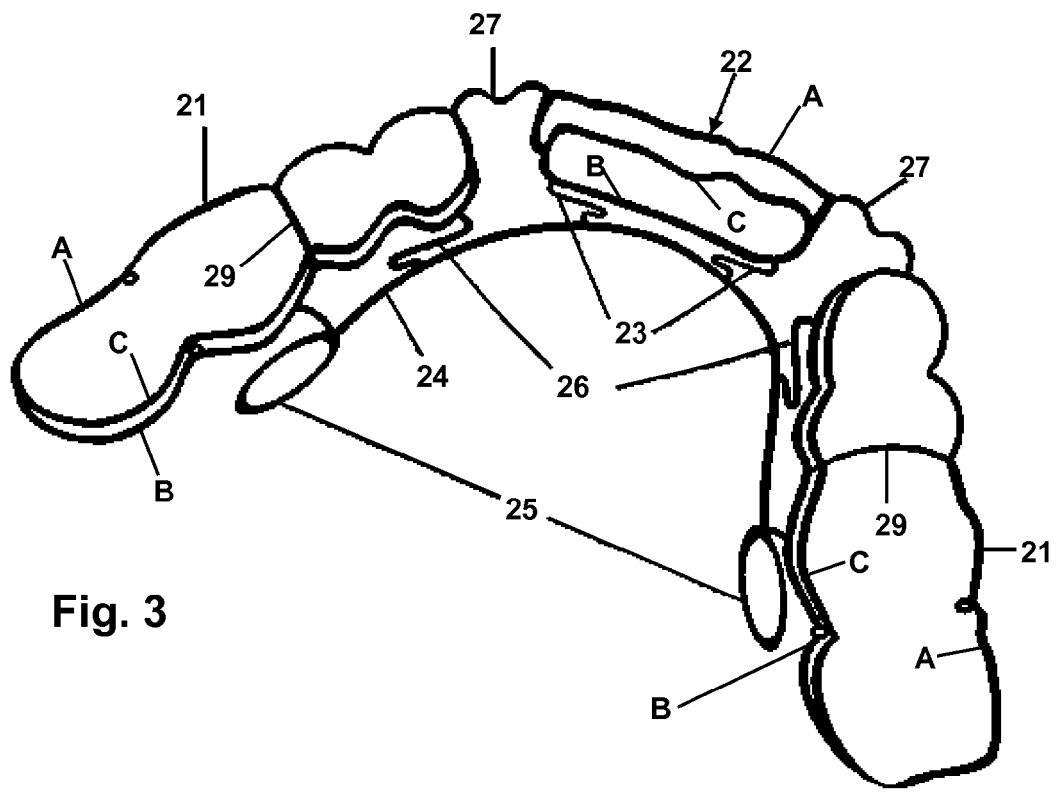

The characteristic feature of the group of inventions is that the metal wireframes are performed of lingual and vestibular details A, B, C located at necks of teeth from the one side and dispersedly mounted along the height of teeth from the other side and connected by crosspieces 29 disposed in interdental spaces. At the same time, lingual (see, FIG. 3) and vestibular (see, FIGS. 1, 2, 4) details of metal wireframes dispersed along the height of teeth are mounted from the side of the teeth facing to the movement direction, namely, in the first case the device is intended for constriction, and in second for expansion of a dental alveolar arch.

A device for correction of the form of dental alveolar arch, in accordance with a first variant is used as follows. After fitting of the device in a cavity of mouth, the patient is trained on peculiarities of treatment with it. The device is activated through every 15-20 days. By activation of lingual (3) and vestibular (4) springs in sagittal and/or transversal directions, as well as, in combination and alternation (proceeding from the clinical indications) with turning of metal wireframes of fastening elements (1) and frontal segment (2) around of their longitudinal axis a correction of the form of dental alveolar arch is achieved.

A device for correction of the form of dental alveolar arch, in accordance with a second variant is used as follows. After fitting of the device in a cavity of a mouth, the patient is trained on peculiarities of treatment with it. The device is activated through every 15-20 days. By activation of a lingual arch (15), its activation units (16), as well as springs (17) and (14) accordingly disposed between a lingual arch (15) and wireframes (11) and (12) in sagittal and/or transversal directions, as well as, in combination and alternation (proceeding from the clinical indications) with turning of metal wireframes of fastening elements (11) and frontal segment (12) around of their longitudinal axis a correction of the form of dental alveolar arch is achieved.

A device for correction of the form of dental alveolar arch, in accordance with a third variant is used as follows. After fitting of the device in a cavity of a mouth, the patient is trained on peculiarities of treatment with it. The device is activated through every 15-20 days. By activation of a lingual arch (24), its activation units (25), springs (27) connecting fastening elements (21) and the wireframe of frontal segment (22), as well as, springs (26) and (23) accordingly disposed between a lingual arch (24) and wireframes (21) and (22) in sagittal and/or transversal directions, as well as, in combination and alternation (proceeding from the clinical indications) with turning of metal wireframes of fastening elements (21) and a frontal segment (22) around of their longitudinal axis a correction of the form of dental alveolar arch is achieved.

Figure 5:
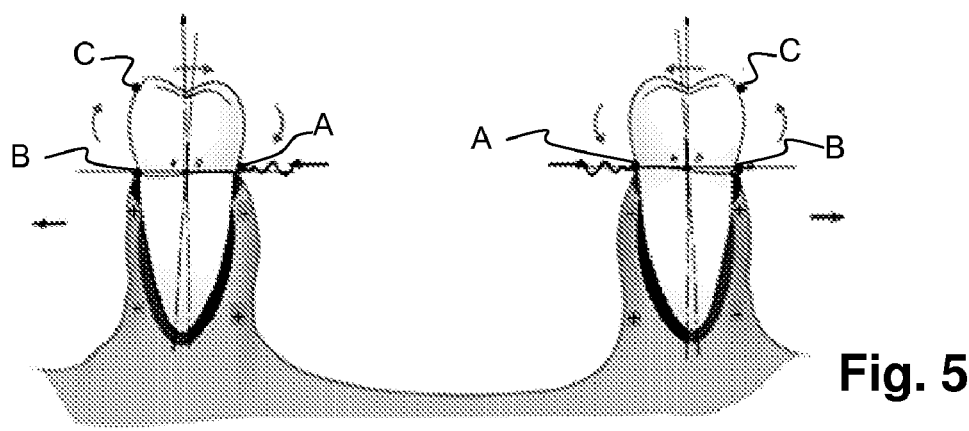
Figure 6:
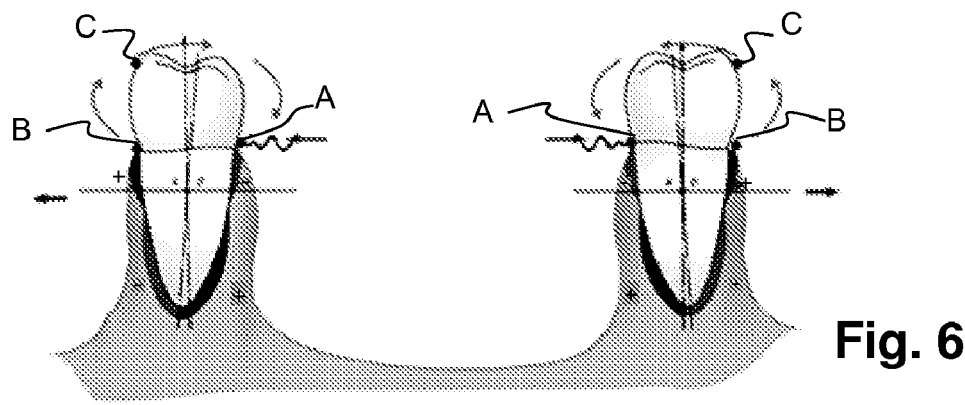
Figure 7:
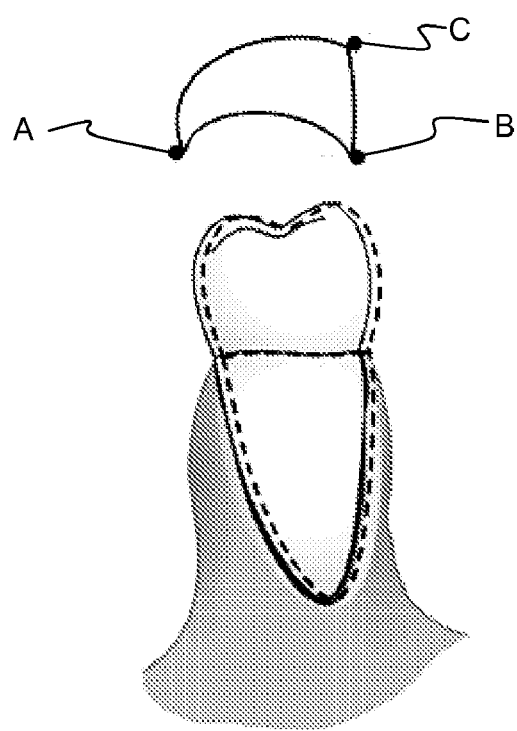

It is well known that the tissue of the alveolar process is a viscous-elastic medium. The tissues of alveolar process (more precisely, periodontium) tolerate vertical loadings relatively well and horizontal loadings much worse. In the Example depicted in FIGS. 5 and 6, a metal wireframe clasps molars at points marked A, B and C. In this example, points A are lingual components of a wireframe and points B and C are vestibular components of the wireframe that are dispersedly mounted along the height of the molars. The wireframes exert forces on the molars and, due to reactions of an alveolar process to these forces, zones of constriction (squeezing) (−) and expansion (tension) (+) are formed accordingly during the expansion and constriction of a dentition. The combination of wireframe forces and reaction of the alveolar process leads to rotary forces on the molar indicated by the curved arrows. Because of the influences of forward and rotary forces on the teeth, a squeezing of the tissues of alveolar process by roots of teeth in horizontal direction occurs that results in its elastic deformation and movement of a tooth. The periodic removal of the device results in partial return of a tooth to an initial position (see, FIG. 7). Changes of directions of forward - rotary forces taking place at the act of chewing promote intensive alternating change of zones of squeezing and tension of the alveolar process. The repeated removals of influences of forward and rotary forces from the teeth between periodic activations of the device, which are combined with an intensive alternating change of zones of squeezing and tension of the alveolar process at the act of chewing, stimulate intensive growth of a bone tissue of alveolar process. Moreover, the frequent removal of the device or its active elements from the oral cavity reduces the influence of elements of the wireframes on the teeth that would tend to push out the teeth from the alveolar socket. The frequent removal of the device or its active elements also increases the forces exerted by the masticatory muscles on separate teeth at the act of chewing, and consequently, prevents a loosening of separate teeth.

Example: A woman of 27 years old with complaints related to cosmetic defect has addressed to the clinic. Objectively: a distal deep bite (malocclusion of class II-1 by Angle), constriction of both dental alveolar arches, irregular position and overcrowding of teeth in a frontal segment.

Two devices have been made and fitted in the cavity of patient's mouth: according to the first variant of the device—for the top teeth line, and according to the second variant of the device—for the lower teeth line.

By activation of a lingual (3) and vestibular (4) springs and wireframes (1) and (2) on the top jaw and by activation of activation units (16) of lingual arch (15), springs (17) and (14) accordingly disposed between a lingual arch (15) and wireframes (1) and (2), as well as, wireframes (11) and (12) on the lower jaw an expansion of dental alveolar arch was ensured. After 3.5 months from the beginning of treatment the measurements of transversal dimensions of dental alveolar arch in the area of 4-th teeth have registered the increase of top and lower jaws, accordingly on 5.0 and 6.5 mm. The position of teeth was considerably normalized, gaps have appeared between teeth that were used in the next months for the correction of teeth position. The growth of the dental alveolar arch in the lateral section of the lower jaw was achieved too. The occlusion was corrected after 6 months. The devices were taken off after 3 months from the beginning of the retention period.

Example: A patient of 19 years old with complaints to cosmetic defect and asymmetry of the face after orthodontic treatment has addressed to the clinic. Objectively: asymmetry of the face, the left side prevailed by its sizes over the right one. The biometric study of jaw models has shown an excess of the transversal sizes of the left side alveolar arch in respect of the palatal suture on 3-5 mm. Compelled compensatory displacement of the lower jaw to the left. The Wilson occlusal plane is inclined downwards from the right to the left.

Two devices for the top and lower teeth lines of the patient have made and fitted in accordance with the third variant of the device for correction of the form of a dental alveolar arch.

During the first 2 months by unilateral activation of activation elements (25) of the arch (24) and springs (23), (26), and a wireframe (21) the increase of the right side of both jaws was achieved. Simultaneously, the correction of the Wilson occlusal curve was realized -dental alveolar contraction of the right segment of the lower jaw. By activation of springs (23), (26) and the wireframe (22) a dental alveolar shift of frontal segments of both jaws to the right was achieved on the $3^{rd}$ month of treatment. During the $4^{th}$ month, the devices were not activated. On $5^{th}$ and $6^{th}$ months by activation of springs (23) and (26), activation units (25) of arch (24), and a wireframe (21) a dental alveolar shift of left lateral segments of both jaws in lingual direction was achieved.

The face asymmetry was considerably diminished after 6 months of the treatment. The devices were taken off after 3 months from the beginning of the retention period.

Practical use of the proposed variants of the devices for correction of the form of dental alveolar arch has shown, that they allow:

to ensure dental alveolar movement of a frontal segment in sagittal-transversal directions,
  to achieve a uniform and/or non-uniform expansion and constriction of a teeth line,
  to ensure successive dental alveolar movement of lateral or frontal segments in different directions,
  to intensify sagittal-transversal movements, both in separate, and simultaneously in several segments of teeth line.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. In the claims that follow, the indefinite article "A", or "An" refers to a quantity of one or more of the item following the article, except where expressly stated otherwise. Any feature, whether preferred or not may be combined with any other feature, whether preferred or not. The appended claims are not to be interpreted as including means-plus-function or step-plus-function limitations, unless such a limitation is explicitly recited in a given claim using the phrase "means for" or "step for".

What is claimed is:

1. A device for correction of the form of dental alveolar arch, comprising: two lateral fastening elements connected through metal lingual and vestibular springs to a frontal fastening element, wherein the lateral and frontal fastening elements are in the form of metal wireframes adapted respectively to directly clasp teeth of a patient's lateral and frontal dentition segments, wherein the metal wireframes include two or more separate wireframe segments respectively adapted to surround two or more corresponding separate dentition segments, each separate dentition segment containing two or more teeth, and wherein each of the two or more separate wireframe segments is comprised of a lingual or vestibular detail adapted to be located at necks of the patient's teeth from one side and two lingual or vestibular details adapted to be dispersedly mounted along the height of crowns of the patient's teeth from the other side, wherein the lingual and vestibular details are connected to each other by crosspieces.

2. A device of claim 1 wherein the lingual or vestibular details of the metal wireframes, which are adapted to be dispersedly mounted along the height of teeth crowns, are configured to be mounted to the teeth from a side of the teeth facing toward a direction of intended movement of the teeth caused by the device.

3. A device of claim 1 wherein one or more of the fastening elements include components disposed on a separate tooth and/or group of teeth of a segment and connected with each other via lingual and/or vestibular springs.

4. The device of claim 1, wherein the two lingual or vestibular details adapted to be dispersedly mounted along the height of teeth crowns include a first wire adapted to be located at the necks of the patient's teeth and a second wire adapted to be located near the top of the crowns of the patient's teeth.

5. A device for correction of the form of dental alveolar arch, comprising: two lateral fastening elements and a frontal fastening element that are connected to a lingual arch, wherein the lateral fastening elements are connected to the lingual arch by activation units and at least one of the lateral fastening elements is additionally connected to the lingual arch by one or more additional springs, wherein the lateral fastening elements and frontal fastening elements are in the form of metal wireframes respectively adapted to directly clasp teeth of a patient's lateral and frontal dentition segments, wherein the metal wireframes include two or more separate wireframe segments respectively adapted to surround two or more corresponding separate dentition segments, each separate dentition segment containing two or more teeth, wherein each of the two or more separate wireframe segments is comprised of a lingual or vestibular detail adapted to be located at necks of the patient's teeth from one side and two lingual or vestibular details adapted to be dispersedly mounted along the height of crowns of the patient's teeth from the other side, wherein the lingual and vestibular details are connected to each other by crosspieces, and wherein the frontal fastening element is connected with the lingual arch directly and/or through springs.

6. A device of claim 5 wherein the lingual or vestibular details of metal wireframes, which are adapted to be dispersedly mounted along the height of teeth, are configured to be mounted to the teeth from a side of the teeth facing toward a direction of intended movement of the teeth caused by the device.

7. A device of claim 5 wherein one or more of the fastening elements include one or more components configured for disposition on a separate tooth and/or group of teeth of a segment and connected with each other via lingual and/or vestibular springs.

8. The device of claim 5 wherein the one or more additional springs is attached to the lingual arch at one or more locations intermediate one of the activation units and a connection between the frontal fastening element and the lingual arch.

9. The device of claim 5, wherein the two lingual or vestibular details adapted to be dispersedly mounted along the height of teeth crowns include a first wire adapted to be located at the necks of the patient's teeth and a second wire adapted to be located near the top of the crowns of the patient's teeth.

10. A device for correction of the form of dental alveolar arch, comprising: two lateral fastening elements and a frontal fastening element that are connected to a lingual arch, wherein the lateral fastening elements are connected to the lingual arch by activation units located at ends of the lingual arch, wherein the lateral fastening elements and frontal fastening element are in the form of metal wireframes respectively adapted to directly clasp teeth of a patient's lateral and frontal dentition segments, wherein the metal wireframes include two or more separate wireframe segments respectively adapted to surround two or more corresponding separate dentition segments, each separate dentition segment containing two or more teeth, wherein each of the two or more separate wireframe segments is comprised of a lingual or vestibular detail adapted to be located at necks of the patient's teeth from one side and two lingual or vestibular details adapted to be dispersedly mounted along the height of crowns of the patient's teeth from the other side, wherein the lingual and vestibular details are connected to each other by crosspieces, wherein the frontal fastening element is connected with the lingual arch through springs, wherein one or more of the lateral fastening elements is connected with the frontal fastening element and additionally connected with the lingual arch through one or more additional springs.

11. A device of claim 10 wherein the lingual or vestibular details of the metal wireframes, which are adapted to be dispersedly mounted along the height of teeth, are adapted to be mounted to the teeth from a side of the teeth facing toward a direction of intended movement of the teeth caused by the device.

12. A device of claim 10 wherein one or more of the fastening elements include components adapted to be disposed on a separate tooth and/or group of teeth of a segment and connected with each other via lingual and/or vestibular springs.

13. The device of claim 10 wherein the one or more additional springs are attached to the lingual arch at a one or more locations intermediate one of the activation units and a point of attachment of one of the springs that connect the frontal fastening element to the lingual arch.

14. The device of claim 10, wherein the two lingual or vestibular details adapted to be dispersedly mounted along the height of teeth crowns include a first wire adapted to be located at the necks of the patient's teeth and a second wire adapted to be located near the top of the crowns of the patient's teeth.

* * * * *